(12) United States Patent
Qian et al.

(10) Patent No.: US 11,992,674 B2
(45) Date of Patent: May 28, 2024

(54) GRAPHENE OXIDE COCHLEAR IMPLANT ELECTRODE AND MANUFACTURING METHOD THEREOF

(71) Applicants: ZHEJIANG NUROTRON BIOTECHNOLOGY CO., LTD., Zhejiang (CN); NANJING DRUM TOWER HOSPITAL, Nanjing (CN)

(72) Inventors: Xiaoyun Qian, Nanjing (CN); Shuqi Qi, Hangzhou (CN); Xia Gao, Nanjing (CN); Xiaoan Sun, Hangzhou (CN); Renjie Chai, Nanjing (CN)

(73) Assignees: ZHEJIANG NUROTRON BIOTECHNOLOGY CO., LTD., Hanhzhou (CN); NANJING DRUM TOWER HOSPITAL, Nanjing (CN)

( * ) Notice: Subject to any disclaimer, the term of this patent is extended or adjusted under 35 U.S.C. 154(b) by 390 days.

(21) Appl. No.: 17/616,572

(22) PCT Filed: Aug. 23, 2019

(86) PCT No.: PCT/CN2019/102226
§ 371 (c)(1),
(2) Date: Dec. 3, 2021

(87) PCT Pub. No.: WO2020/244062
PCT Pub. Date: Dec. 10, 2020

(65) Prior Publication Data
US 2022/0233847 A1    Jul. 28, 2022

(30) Foreign Application Priority Data
Jun. 3, 2019  (CN) .......................... 201910474794.8

(51) Int. Cl.
*A61N 1/05*   (2006.01)
*A61N 1/36*   (2006.01)

(52) U.S. Cl.
CPC ....... *A61N 1/0541* (2013.01); *A61N 1/36038* (2017.08)

(58) Field of Classification Search
CPC .............. A61N 1/0541; A61N 1/39036–36039
See application file for complete search history.

(56) References Cited

U.S. PATENT DOCUMENTS

| | | | |
|---|---|---|---|
| 6,615,483 B2 | 9/2003 | Lindegren | |
| 2017/0326381 A1* | 11/2017 | Kozai | .................. A61N 1/0551 |

(Continued)

FOREIGN PATENT DOCUMENTS

| | | |
|---|---|---|
| CN | 101744671 | 6/2010 |
| CN | 101879107 | 11/2010 |

(Continued)

*Primary Examiner* — Eric D. Bertram
(74) *Attorney, Agent, or Firm* — Jiwen Chen; Joywin IP Law PLLC

(57) ABSTRACT

Disclosed are a graphene oxide cochlear implant electrode and a manufacturing method thereof. The graphene oxide cochlear implant electrode includes an electrode tip, an electrode carrier, electrode contacts, a first positioning ring, a second positioning ring, a boosting portion, an electrode wire, a loop electrode, a loop electrode wire and a wire array, herein the electrode tip is arranged at a foremost portion of the cochlear implant electrode, the electrode carrier is silica gel grafted with a graphene oxide, the electrode carrier wraps the electrode wire and semi-wraps the electrode contacts connected to the electrode wire one by one, and the electrode carrier is slightly curved as a whole; and the electrode wire is connected to the electrode contacts one by one and forms a spiral shape through the first positioning ring, the second positioning ring and the boosting portion. Methyl vinyl silica gel is adopted, and after activation treatment, the graphene oxide is grafted to the silica gel through a silane coupling agent trimethoxysilane, as to form a hydrophilic antibacterial polymer, not only the hydrophi- (Continued)

licity of the silica gel is improved, but also the silica gel is endowed with an antibacterial property, and the cytotoxicity thereof is reduced at the same time.

6 Claims, 3 Drawing Sheets

(56) References Cited

U.S. PATENT DOCUMENTS

| | | | | |
|---|---|---|---|---|
| 2019/0143100 | A1* | 5/2019 | Tourrel | H05K 1/118 |
| | | | | 607/137 |
| 2021/0038773 | A1* | 2/2021 | Cui | A61B 5/268 |
| 2021/0038883 | A1* | 2/2021 | Racz | A61N 1/36038 |
| 2022/0226639 | A1* | 7/2022 | Qian | A61N 1/0541 |

FOREIGN PATENT DOCUMENTS

| | | |
|---|---|---|
| CN | 107880305 | 4/2018 |
| CN | 108837301 | 11/2018 |

* cited by examiner

```
┌─────────────────────────────────────────────────────────────┐   S10
│ Manufacturing an electrode contacts: annealing a platinum-  │
│ iridium alloy blank, and rolling same into a platinum-      │
│ iridium alloy sheet; and after laser-cutting the platinum-  │
│ iridium alloy sheet, punch-forming.                         │
└─────────────────────────────────────────────────────────────┘
                              │
                              ▼
┌─────────────────────────────────────────────────────────────┐   S20
│ Manufacturing an electrode wire: annealing, cold-drawing    │
│ and straightening the platinum-iridium alloy blank into a   │
│ platinum-iridium alloy wire; performing wave-shaped         │
│ treatment on the platinum-iridium alloy wire, namely the    │
│ electrode wire; and welding the electrode contacts with the │
│ electrode wire, ultrasonic-cleaning and plasma-treating.    │
└─────────────────────────────────────────────────────────────┘
                              │
                              ▼
┌─────────────────────────────────────────────────────────────┐   S30
│ Manufacturing a loop electrode: annealing, cold-drawing,    │
│ straightening, and grinding the platinum-iridium alloy      │
│ blank into a ring-shaped platinum-iridium alloy sheet; and  │
│ laser-cutting and deburring.                                │
└─────────────────────────────────────────────────────────────┘
                              │
                              ▼
┌─────────────────────────────────────────────────────────────┐   S40
│ Manufacturing a loop electrode wire: annealing, cold-       │
│ drawing and straightening the platinum-iridium alloy blank  │
│ into a platinum-iridium alloy wire, namely the loop         │
│ electrode wire.                                             │
└─────────────────────────────────────────────────────────────┘
                              │
                              ▼
┌─────────────────────────────────────────────────────────────┐   S50
│ Arranging the electrode contacts, the electrode wire, the   │
│ loop electrode and the loop electrode wire, bundling and    │
│ spiraling the electrode wire, and injection-molding by      │
│ using graphene oxide silica gel.                            │
└─────────────────────────────────────────────────────────────┘
                              │
                              ▼
┌─────────────────────────────────────────────────────────────┐   S60
│ Laser-cutting an exposed surface of the electrode contacts, │
│ and cutting a ring surface of the loop electrode; and       │
│ cleaning and electrical-inspecting.                         │
└─────────────────────────────────────────────────────────────┘
```

FIG. 4

GRAPHENE OXIDE COCHLEAR IMPLANT ELECTRODE AND MANUFACTURING METHOD THEREOF

This is a U.S. national stage application of PCT Application No. PCT/CN2019/102226 under 35 U.S.C. 371, filed Aug. 23, 2019 in Chinese, claiming priority of Chinese Application No. 201910474794.8, filed Jun. 3, 2019, all of which is hereby incorporated by reference.

TECHNICAL FIELD

The present invention relates to the field of electronic medical treatment, in particular to a graphene oxide cochlear implant electrode and a manufacturing method thereof.

BACKGROUND TECHNOLOGY

Medical silica gel belongs to a family of organopolysiloxane, and is formed by polymerization of monomers composed of silicon, oxygen and an organic radical. The medical silica gel has good physical and chemical stability and physiological inertia. After being implanted in a human body, it may be absorbed, metabolized and degraded by the body, and it has good aging resistance under complex environmental conditions in vivo. These excellent characteristics of the medical silica gel make it increasingly widely used in the biomedical field. The medical silica gel began to be used in the medical field in the middle of the 20th century, and is more widely used in implant materials at present, such as an artificial heart valve, a urinary catheter, a retina and other organ or tissue substitutes. However, because the surface of the medical silica gel shows the strong hydrophobicity, it has poor affinity with the body after being implanted in the body, a tissue forms an envelope around it, and after the envelope is stimulated by an external environment, it is easy to cause contracture so that problems such as deformation and displacement of an implant and material exposure occurred. In addition, while the medical silica gel contacts with an internal tissue of the human body, the surface thereof is prone to produce bacterial adhesion, thereby a biofilm is formed, as to cause an infection and various complications, so that a patient suffers a great pain. Therefore, improving the antibacterial property of the medical silica gel is an effective means to expand a clinical application range thereof.

In order to improve the surface hydrophilicity of the medical silica gel and thereby improve its affinity with the body, various methods are used to modify the medical silica gel in an existing technology. At present, the more commonly used methods include: surface-grafted modification, plasma surface modification, nano-material filling medical silica gel modification, biomimetic method modification, and medical silica gel modification by mixing with bioactive substance and the like. In order to reduce the bacterial infection caused by the medical silica gel implantation as much as possible, people usually treat the surface of the medical silica gel, for example, the surface of a medical silica gel material is coated with an antibacterial ingredient, or an antibacterial agent is grafted to the surface of the medical silica gel to form antibiosis by a chemical grafting method. However, the antibiosis, formed by the commonly used antibacterial agents such as a metallic silver ion, may effectively prevent bacterial adhesion and proliferation, but also has potential danger such as cytotoxicity at the same time, and applications thereof are limited to a certain extent.

SUMMARY OF THE INVENTION

A technical problem to be solved by the present invention is to provide a graphene oxide cochlear implant electrode that improves hydrophilicity of a silica gel surface, imparts an antibacterial property to silica gel, and reduces its cytotoxicity and a manufacturing method thereof.

In order to achieve the above objects, a technical scheme of the present invention is as follows: a graphene oxide cochlear implant electrode, comprising an electrode tip, an electrode carrier, electrode contacts, a first positioning ring, a second positioning ring, a boosting portion, an electrode wire, a loop electrode, a loop electrode wire and a wire array.

Wherein, the electrode tip is arranged at a foremost portion of the cochlear implant electrode, the electrode carrier is silica gel grafted with a graphene oxide, the electrode carrier wraps the electrode wire and semi-wraps the electrode contacts connected to the electrode wire one by one, and the electrode carrier is slightly curved as a whole; the first positioning ring, the second positioning ring and the boosting portion are arranged sequentially behind all of the electrode contacts, and are used for insertion depth positioning and implantation assistance during implantation; the electrode wire is connected to the electrode contacts one by one and forms a spiral shape through the first positioning ring, the second positioning ring and the boosting portion, the loop electrode is arranged behind the spiral electrode wire and is ring-shaped; and the loop electrode wire is connected to the loop electrode, the wire array is composed of the electrode wire, and one end of the wire array and one end of the loop electrode wire are exposed out of the electrode carrier.

Preferably, the electrode contacts are hook-shaped electrodes each having hooking positions provided with a first lateral hole and a second lateral hole, and a bottom inner side connected to the electrode wire by means of a welding spot.

Preferably, the electrode contacts are inner-U-shaped.

Corresponding to the above graphene oxide cochlear implant electrode, the present invention further provides a manufacturing method for the graphene oxide cochlear implant electrode, comprising the following steps.

S10, manufacturing electrode contacts: annealing a platinum-iridium alloy blank, and rolling the same into a platinum-iridium alloy sheet; and after laser-cutting the platinum-iridium alloy sheet, punch-forming.

S20, manufacturing an electrode wire: annealing, cold-drawing and straightening the platinum-iridium alloy blank into a platinum-iridium alloy wire; performing wave-shaped treatment on the platinum-iridium alloy wire, namely the electrode wire; and welding the electrode contacts with the electrode wire, ultrasonic-cleaning and plasma-treating.

S30, manufacturing a loop electrode: annealing, cold-drawing, straightening, and grinding the platinum-iridium alloy blank into a ring-shaped platinum-iridium alloy sheet; and laser-cutting and deburring.

S40, manufacturing a loop electrode wire: annealing, cold-drawing and straightening the platinum-iridium alloy blank into a platinum-iridium alloy wire, namely the loop electrode wire.

S50, arranging the electrode contacts, the electrode wire, the loop electrode and the loop electrode wire, bundling and spiraling the electrode wire, and injection-molding by using graphene oxide silica gel.

S60, laser-cutting exposed surfaces of the electrode contacts, and cutting a ring surface of the loop electrode; and cleaning and electrical-inspecting.

Herein, the manufacture of the graphene oxide silica gel includes the following steps.

S51, putting a silica gel sheet in deionized water, acetone and ethanol and ultrasonic-cleaning for 15-20 min, as to remove impurities such as an oil stain on the surface of silicone rubber, rinsing with the deionized water, and air-drying for later use.

S52, suspending the cleaned silica gel sheet in an ultraviolet lamp box with a wavelength of 272 nm and irradiating for 2 hours, as to activate the surface thereof, and generating an active group.

S53, under a condition of 50° C. of a constant temperature, putting the ultraviolet-irradiated silica gel sheet in silane coupling agent solution and soaking for 1~1.5 hours, rinsing with absolute ethanol after being taken out, as to remove a silane coupling agent physically adsorbed on the surface, and air-drying for later use.

S54, putting the silica gel sheet in graphene oxide aqueous dispersion and soaking for 1~4 hours, as to obtain the silica gel sheet grafted with the graphene oxide.

Preferably, the manufacturing of the electrode contacts further includes laser-punching both sides of the platinum-iridium alloy sheet.

Preferably, the silane coupling agent is trimethoxysilane.

The graphene oxide cochlear implant electrode adopting the above technical scheme at least includes the following beneficial effects.

I. The overall shape of the slightly curved electrode is combined with two positioning rings and the boosting portion, it is more convenient during an implantation process, less damage to a cochlea, and does not cause unnecessary distortion of the electrode as a whole.

II. The combination of the electrode contacts with the lateral holes and the silica gel is stronger, and not easy to fall off, and an exposed area of the electrode contacts is appropriate.

III. The graphene oxide is added to the electrode carrier, and the methyl vinyl silica gel is used as a substrate. The surface of the silica gel is firstly activated by the ultraviolet radiation, and then the graphene oxide is grafted to the silica gel by the silane coupling agent trimethoxysilane. It not only improves the hydrophilicity of the silica gel, but also imparts the antibacterial property to the silica gel, while its cytotoxicity is reduced, so that the antibacterial property, reliability and safety of the cochlear implant electrode are greatly improved, it is guaranteed that the implanted electrode may work normally in the human body for a long time, and it has a promotion effect on a cochlear implant manufacturing technology.

BRIEF DESCRIPTION OF THE DRAWINGS

FIG. 4 is a flow diagram of steps of a manufacturing method for the graphene oxide cochlear implant electrode in an embodiment of the method of the present invention.

DETAILED DESCRIPTION OF THE EMBODIMENTS

Figure 1:
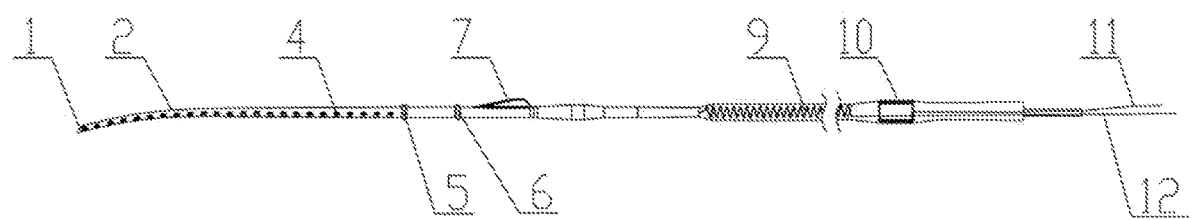
FIG. 1 is a structure schematic diagram of a graphene oxide cochlear implant electrode in an embodiment of the present invention.
Figure 2:
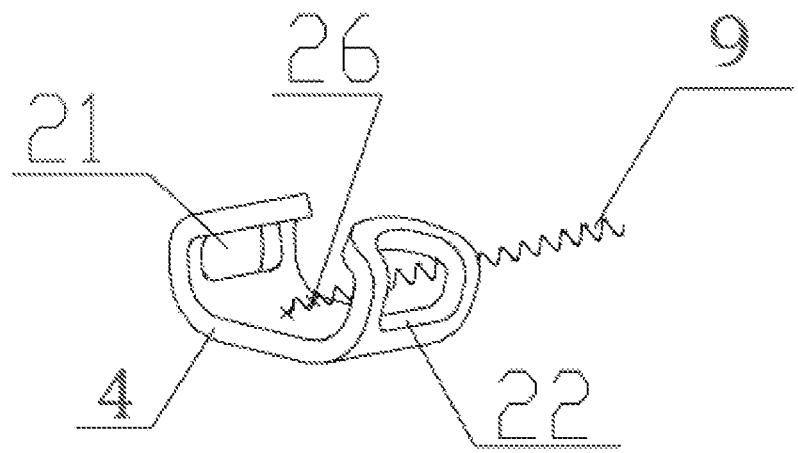
FIG. 2 is a structure schematic diagram of electrode contacts (inner-U-shaped electrode) of the graphene oxide cochlear implant electrode in an embodiment of the present invention.
Figure 3:
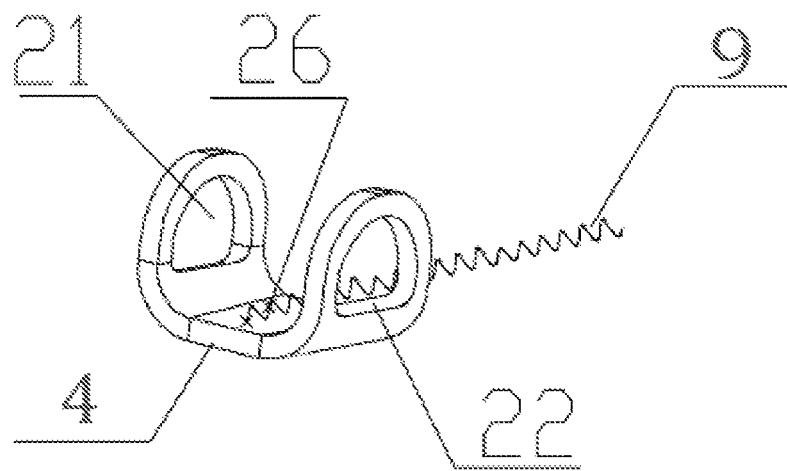
FIG. 3 is a structure schematic diagram of electrode contacts (hook-shaped electrode) of the graphene oxide cochlear implant electrode in another embodiment of the present invention.

As shown in FIGS. 1-3, a graphene oxide cochlear implant electrode, including an electrode tip 1, an electrode carrier 2, electrode contacts 4, a first positioning ring 5, a second positioning ring 6, a boosting portion 7, an electrode wire 9, a loop electrode 10, a loop electrode wire 11 and a wire array 12.

Herein, the electrode tip 1 is arranged at a foremost portion of the cochlear implant electrode, the electrode carrier 2 is silica gel grafted with a graphene oxide, the electrode carrier 2 wraps the electrode wire 9 and semi-wraps the electrode contacts 4 connected to the electrode wire 9 one by one, and the electrode carrier 2 is slightly curved as a whole; the first positioning ring 5, the second positioning ring 6 and the boosting portion 7 are arranged sequentially behind all of the electrode contacts 4, and are used for insertion depth positioning and implantation assistance during implantation; the electrode wire 9 is connected to the electrode contacts 4 one by one and forms a spiral shape through the first positioning ring 5, the second positioning ring 6 and the boosting portion 7, the loop electrode 10 is arranged behind the spiral electrode wire 9 and is ring-shaped; and the loop electrode wire 11 is connected to the loop electrode 10, the wire array 12 is composed of the electrode wire 9, and one end of the wire array 12 and one of the loop electrode wire 11 are exposed out of the electrode carrier 2.

Referring to FIG. 2, the electrode contacts 4 are inner-U-shaped each having hooking positions provided with a first lateral hole 21 and a second lateral hole 22, and a bottom inner side connected to the electrode wire 9 by means of a welding spot 26.

Referring to FIG. 3, the electrode contacts 4 are hook-shaped each having two hooking sides provided with a first lateral hole 21 and a second lateral hole 22, and a bottom inner side connected to the electrode wire 9 by means of a welding spot 26, and the angle of the hook shape is 25-135°.

The electrode contacts 4 with the lateral holes are more firmly combined with the electrode carrier 2, the area of the electrode contacts 4 exposed outside the electrode carrier 2 is also very suitable, and the effect of electrical stimulation is also improved.

The electrode carrier is the silica gel grafted with the graphene oxide, and has the antibacterial property. The antibacterial properties of the blank silica gel and the silica gel grafted with the graphene oxide are qualitatively evaluated against *Escherichia coli* and *Staphylococcus aureus* by a plate colony counting method and a fluorescent staining method. Bacteria are cultured on the surface of the silica gel grafted with the graphene oxide as an experimental group, and bacteria are cultured on the surface of the blank silica gel as a control group. After the *Escherichia coli* are contact-cultured with the silica gel grafted with the graphene oxide, bacterial colonies are significantly less than the control group, and the antibacterial rate is 88.7%; and after the *Staphylococcus aureus* are contact-cultured with the silica gel grafted with the graphene oxide, the bacterial colonies thereof are also reduced compared to the control group, and the antibacterial rate is 65%. Therefore, the silica gel grafted with the graphene oxide shows the antibacterial property against both gram-negative bacteria and gram-positive bacteria.

The silica gel used in the cochlear implant electrode in an existing technology has poor hydrophilicity and shows strong hydrophobicity. Therefore, the affinity after implantation in the cochlea is poor. While it comes in contact with the internal tissue of the human body, the surface thereof is prone to produce the bacterial adhesion, thereby a biofilm is formed, as to cause an infection and various complications. The silica gel grafted with the graphene oxide has excellent dispersibility in water due to hydrophilic groups such as a hydroxyl and a carboxyl attached to defects of the graphene oxide, and it greatly improves the hydrophilicity of the silica gel. In addition, the silica gel grafted with the graphene oxide is used as the electrode carrier, the larger surface area may be used as a drug carrier, and drug molecules may be grafted to a silica gel active group of the graphene oxide, so functionalized graphene oxide silica gel with good water solubility and biocompatibility may be manufactured. The functionalized graphene oxide silica gel is not limited to the implantation in the human body, but may also graft molecules with other functions onto the graphene oxide, so that it has various functions, such as purifying the environment and adsorbing toxic and harmful substances in water.

Corresponding to the above electrode, an embodiment of the method of the present invention refers to FIG. 4, a manufacturing method for the graphene oxide cochlear implant electrode, including the following steps.

S10, manufacturing electrode contacts: annealing a platinum-iridium alloy blank, and rolling same into a platinum-iridium alloy sheet; and after laser-cutting the platinum-iridium alloy sheet, punch-forming.

S20, manufacturing an electrode wire: annealing, cold-drawing and straightening the platinum-iridium alloy blank into a platinum-iridium alloy wire; performing wave-shaped treatment on the platinum-iridium alloy wire, namely the electrode wire; and welding the electrode contacts with the electrode wire, ultrasonic-cleaning and plasma-treating.

S30, manufacturing a loop electrode: annealing, cold-drawing, straightening, and grinding the platinum-iridium alloy blank into a ring-shaped platinum-iridium alloy sheet; and laser-cutting and deburring.

S40, manufacturing a loop electrode wire: annealing, cold-drawing and straightening the platinum-iridium alloy blank into a platinum-iridium alloy wire, namely the loop electrode wire.

S50, arranging the electrode contacts, the electrode wire, the loop electrode and the loop electrode wire, bundling and spiraling the electrode wire, and injection-molding by using graphene oxide silica gel.

S60, laser-cutting exposed surfaces of the electrode contacts, and cutting a ring surface of the loop electrode; and cleaning and electrical-inspecting.

Herein, the manufacture of the graphene oxide silica gel comprises the following steps.

S51, putting a silica gel sheet in deionized water, acetone and ethanol and ultrasonic-cleaning for 15-20 min, as to remove impurities such as an oil stain on the surface of silicone rubber, rinsing with the deionized water, and air-drying for later use.

S52, suspending the cleaned silica gel sheet in an ultraviolet lamp box with a wavelength of 272 nm and irradiating for 2 hours, as to activate the surface thereof, and generating an active group.

S53, under a condition of 50° C. of a constant temperature, putting the ultraviolet-irradiated silica gel sheet in silane coupling agent solution and soaking for 1~1.5 hours, rinsing with absolute ethanol after being taken out, as to remove a silane coupling agent physically adsorbed on the surface, and air-drying for later use.

S54, putting the silica gel sheet in graphene oxide aqueous dispersion and soaking for 1~4 hours, as to obtain the silica gel sheet grafted with the graphene oxide.

In a specific embodiment, S10 of manufacturing the electrode contacts further includes laser-punching both sides of the platinum-iridium alloy sheet.

The silica gel adopts methyl vinyl, the surface of the silica gel is activated by ultraviolet radiation firstly, and then the graphene oxide is grafted onto the silica gel by the silane coupling agent trimethoxysilane. The method is simple and easy to achieve, and it not only immerses the silica gel in graphene oxide suspension, the grafting effect is good, and the content is high.

Finally, it is to be noted that the above preferred embodiments are only used to illustrate the technical scheme of the present invention and not to limit them. Although the present invention is described in detail through the above preferred embodiments, those skilled in the art should understand that various changes may be made to it in the form and details without departing from a scope defined by the claims of the present invention.

The invention claimed is:

1. A graphene oxide cochlear implant electrode, comprising an electrode tip, an electrode carrier, electrode contacts, a first positioning ring, a second positioning ring, a boosting portion, an electrode wire, a loop electrode, a loop electrode wire and a wire array, wherein,
   the electrode tip is arranged at a foremost portion of the cochlear implant electrode, the electrode carrier is silica gel grafted with a graphene oxide, the electrode carrier wraps the electrode wire and semi-wraps the electrode contacts connected to the electrode wire one by one, and the electrode carrier is slightly curved as a whole; the first positioning ring, the second positioning ring and the boosting portion are arranged sequentially behind all of the electrode contacts, and are used for insertion depth positioning and implantation assistance during implantation; the electrode wire is connected to the electrode contacts one by one and forms a spiral shape through the first positioning ring, the second positioning ring and the boosting portion, the loop electrode is arranged behind the spiral electrode wire and is ring-shaped; and the loop electrode wire is connected to the loop electrode, the wire array is composed of the electrode wire, and one end of the wire array and one end of the loop electrode wire are exposed out of the electrode carrier.

2. The graphene oxide cochlear implant electrode according to claim 1, wherein the electrode contacts are hook-shaped electrodes each having hooking positions provided with a first lateral hole and a second lateral hole, and a bottom inner side connected to the electrode wire by means of a welding spot.

3. The graphene oxide cochlear implant electrode according to claim 1, wherein the electrode contacts are inner-U-shaped.

4. A manufacturing method for the graphene oxide cochlear implant electrode according to claim 1, comprising the following steps:
   S10, manufacturing electrode contacts: annealing a platinum-iridium alloy blank, and rolling same into a platinum-iridium alloy sheet; and after laser-cutting the platinum-iridium alloy sheet, punch-forming;
   S20, manufacturing an electrode wire: annealing, cold-drawing and straightening the platinum-iridium alloy blank into a platinum-iridium alloy wire; performing wave-shaped treatment on the platinum-iridium alloy wire, namely the electrode wire; and welding the electrode contacts with the electrode wire, ultrasonic-cleaning and plasma-treating;

S30, manufacturing a loop electrode: annealing, cold-drawing, straightening, and grinding the platinum-iridium alloy blank into a ring-shaped platinum-iridium alloy sheet; and laser-cutting and deburring;

S40, manufacturing a loop electrode wire: annealing, cold-drawing and straightening the platinum-iridium alloy blank into a platinum-iridium alloy wire, namely the loop electrode wire;

S50, arranging the electrode contacts, the electrode wire, the loop electrode and the loop electrode wire, bundling and spiraling the electrode wire, and injection-molding by using graphene oxide silica gel; and S60, laser-cutting exposed surfaces of the electrode contacts, and cutting a ring surface of the loop electrode; and cleaning and electrical-inspecting;

wherein, the manufacture of the graphene oxide silica gel comprises the following steps:

S51, putting a silica gel sheet in deionized water, acetone and ethanol and ultrasonic-cleaning for 15-20 min, as to remove impurities such as an oil stain on the surface of silicone rubber, rinsing with the deionized water, and air-drying for later use;

S52, suspending the cleaned silica gel sheet in an ultraviolet lamp box with a wavelength of 272 nm and irradiating for 2 hours, as to activate the surface thereof, and generating an active group;

S53, under a condition of 50° C. of a constant temperature, putting the ultraviolet-irradiated silica gel sheet in silane coupling agent solution and soaking for 1-1.5 hours, rinsing with absolute ethanol after being taken out, as to remove a silane coupling agent physically adsorbed on the surface, and air-drying for later use; and S54, putting the silica gel sheet in graphene oxide aqueous dispersion and soaking for 1-4 hours, as to obtain the silica gel sheet grafted with the graphene oxide.

5. The manufacturing method for the graphene oxide cochlear implant electrode according to claim 4, wherein the manufacturing of the electrode contacts further comprises laser-punching both sides of the platinum-iridium alloy sheet.

6. The manufacturing method for the graphene oxide cochlear implant electrode according to claim 4, wherein the silane coupling agent is trimethoxysilane.

* * * * *